United States Patent
Corvin

(10) Patent No.: US 7,953,650 B2
(45) Date of Patent: May 31, 2011

(54) MEDICAL DIAGNOSTIC SYSTEM ACQUISITION AND FINANCING METHOD AND APPARATUS

(75) Inventor: Christoph T. Corvin, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 2529 days.

(21) Appl. No.: 09/747,040

(22) Filed: Dec. 22, 2000

(65) Prior Publication Data

US 2003/0046197 A1    Mar. 6, 2003

(51) Int. Cl.
    *G06Q 40/00*    (2006.01)
(52) U.S. Cl. .................. 705/35; 705/41; 705/44
(58) Field of Classification Search .............. 705/35, 705/41, 44
    See application file for complete search history.

(56) References Cited

U.S. PATENT DOCUMENTS

| | | | | |
|---|---|---|---|---|
| 5,590,038 A | * | 12/1996 | Pitroda | 395/241 |
| 5,644,778 A | * | 7/1997 | Burks et al. | 705/2 |
| 6,038,551 A | * | 3/2000 | Barlow et al. | 705/41 |
| 6,167,385 A | * | 12/2000 | Hartley-Urquhart | 705/35 |
| 6,260,024 B1 | * | 7/2001 | Shkedy | 705/37 |
| 6,493,724 B1 | * | 12/2002 | Cusack et al. | 707/104.1 |
| 6,578,074 B1 | * | 6/2003 | Bahlmann | 709/220 |
| 6,735,569 B1 | * | 5/2004 | Wizig | 705/4 |
| 6,751,630 B1 | * | 6/2004 | Franks et al. | 707/102 |
| 6,757,898 B1 | * | 6/2004 | Ilsen et al. | 709/203 |

OTHER PUBLICATIONS

McCormack, J., "A Worldwide Network of Supplies", Health Care Management, p. 54-60 (Jul. 1999).*
Kalbhen, J., "Buying on the Web: A Site-Seers Guide"; Materials Management in Health Care, vol. 8, No. 7 (Jul. 1999).*

* cited by examiner

*Primary Examiner* — Daniel S Felten

(74) *Attorney, Agent, or Firm* — Fletcher Yoder

(57) ABSTRACT

The present technique is associated with financial analysis of a transaction for medical resources. The technique allows a client to interact with a remote financial analysis system via a network interface, and to enter and transmit client data associated with a desired transaction to the financial analysis system for a transaction analysis. Accordingly, the client receives multiple transaction options tailored to the desired transaction and the client data.

56 Claims, 6 Drawing Sheets

```
          124              210
           |                |
  128  ┌──(TM) COMPANY NAME ─122         126─ SERVICE ─┐
       │ HOME │PAGE 1│PAGE 2│PAGE 3│PAGE 4│PAGE 5│PAGE 6│PAGE 7│ HELP │
                                                                   130
  EXISTING CUSTOMER: ─212
      FIRST NAME: ─228  [FN1] ─216    248─ USER ID:   [ID1] ─240
  232 LAST NAME: ─230   [LN1] ─218    250─ PASSWORD:  [PW1] ─242
      INSTITUTION NAME: [IN1] ─220    252─ BILLING #: [BN1] ─244
      ADDRESS: ─234     [ADDRESS1] ─222
      CITY: [CITY1]   STATE: [S1▼]─226  254─ ZIP CODE: [ZIP1] ─246
       236   224    238
  NEW CUSTOMER: ─214
      FIRST NAME: ─268  [FN2] ─256    288─ PHONE #:    [PN1] ─280
  272 LAST NAME: ─270   [LN2] ─258    290─ E-MAIL:     [EM1] ─282
      INSTITUTION NAME: [IN2] ─260    292─ REFERRED BY:[REF1]─284
      ADDRESS: ─274     [ADDRESS2]─262
      CITY: [CITY2]   STATE: [S2▼]─266  294─ ZIP CODE: [ZIP2] ─286
       276   264    278
                                    ┌─────────────┐
                                    │  CONTINUE   │
                                    │ TO PRODUCTS │─296
                                    └─────────────┘
```

FIG. 6

```
          124         420
           |           |
  128  ┌──(TM) COMPANY NAME ─122         126─ SERVICE ─┐
       │ HOME │PAGE 1│PAGE 2│PAGE 3│PAGE 4│PAGE 5│PAGE 6│PAGE 7│ HELP │
  424─PRE-    426      428      430                432      130
      APPROVED SELECT  TERM     DESCRIPTION        PAYMENTS
       NO      ☐─440   TERM 1   INSTALLMENT LOAN    PMT 1
       NO      ☐─442   TERM 2   OPER. LEASE ─434    PMT 2
       NO      ☐─444   TERM 3   OPER. LEASE ─436    PMT 3
                                WITH SERVICE ─438
       YES     ☐─446   TERM 4   PACKAGE 4           PMT 4
       YES     ☒─448   TERM N   PACKAGE N           PMT N

┌──────────┐ ┌────────────┐ ┌──────────┐ ┌────────────┐
   │  PRINT   │ │  CONTACT   │ │ CONTACT  │ │   SUBMIT   │
   │  QUOTES  │ │   SALES    │ │    ME    │ │ APPLICATION│
   └──────────┘ │REPRESENT.  │ └──────────┘ └────────────┘
                └────────────┘
       462          456            458          460
```

128 ™ COMPANY NAME —122  126 — SERVICE

| HOME | PAGE 1 | PAGE 2 | PAGE 3 | PAGE 4 | PAGE 5 | PAGE 6 | PAGE 7 | HELP |

EQUIPMENT —300   308 QTY   310 $ 130 AMOUNT

- 324 PRODUCT/SERVICE TYPE: [SYSTEM 1 ▼] ~312   [Q1]   [COST 1]
- 326 MANUFACTURER: [MANUF 1 ▼] ~314       334       336
- 328 MODEL NUMBER: [MODEL 1 ▼] ~316
- 330 DESCRIPTION: [DESC1] ~318
- 332 DESIRED DELIVERY: [MONTH ▼] [YEAR ▼]
  320        322

OPTIONS & ACCESSORIES —302   338   342   346
- OPTION 1: [OPTION 1 ▼]   [Q2]   [COST 2]
- OPTION N: [OPTION N ▼]   [Q3]   [COST 3]
       340  344  348

SERVICES —304   350   358   366   364
- TRAINING: 352 [SERVICE PLAN 1 ▼]   [TERM 1]   [COST 4]
- 356 SERVICE 2: [SERVICE PLAN 2 ▼] 360 [TERM 2]   [COST 5]
- SERVICE N: [SERVICE PLAN N ▼]   [TERM 3]   [COST 6]
       354       362       368

TRADE-INS —306       382   386
- PRODUCT 1: [PRODUCT 1 ▼] ~370   [Q4]   [CREDIT 1]
- 378 PRODUCT N: [PRODUCT N ▼] ~372   [Q5]   [CREDIT 2]
- AUTHORIZATION # [AUTH 1] ~374
- CONTACT NAME [CONTACT 1] ~376   384   388
380

☒ SAVE —392
390 ☒ CONTACT ME

[ORDER]  [GET MULTIPLE FINANCING QUOTES]  [CONTACT SALES REP.]

394   396   414   FIG. 7   416   418

MEDICAL DIAGNOSTIC SYSTEM ACQUISITION AND FINANCING METHOD AND APPARATUS

FIELD OF THE INVENTION

The present invention relates generally to financial analysis systems and, more particularly, to a technique for providing a plurality of transaction options for medical resources for a medical facility. The present technique permits data exchange between a financial analysis system and a remote interface via a network, allowing a client to interact with the financial analysis system and to receive transaction options based on client data.

BACKGROUND OF THE INVENTION

Medical institutions require various medical resources, such as real estate, human resources, medical systems, equipment and instruments, to provide healthcare services to patients. The medical resources employed at a particular medical institution greatly impact the efficiency, cost and revenue associated with a desired medical procedure. For example, a current system may allow a procedure to be completed in 20 minutes with 10 minutes of setup time, while another system may complete the procedure in 10 minutes with only 2 minutes of setup time. Less time means more procedures, and thus more revenue and lower patient waiting time for the procedures. As medical technology advances, particularly in the area of electronics and computer aided instruments, medical institutions must evaluate the feasibility of investing in new, additional or upgraded medical resources to better serve patients and become more efficient and profitable.

For example, medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. In many instances, these modalities complement one another and offer the physician a range of techniques for imaging particular types of tissue, organs, physiological systems, and so forth. Health care institutions often dispose of several such imaging systems at a single or multiple facilities, permitting its physicians to draw upon such resources as required by particular patient needs.

Modern medical diagnostic systems typically include circuitry for acquiring image data and for transforming the data into a useable form which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. However, medical resources such as the above systems may become outdated, or relatively inefficient and costly compared to current medical systems. Accordingly, a medical institution may desire an upgraded medical system, or other new medical resources, such as medical products, systems and services offered by a medical resource supplier. If sufficient internal funds are available, the medical institution may simply purchase the desired medical resource with those funds. Alternatively, the medical institution may obtain third party financing (e.g., a term loan), financing from the seller (e.g., an installment loan), or leasing from the seller (e.g., an operating lease). Unfortunately, the seller may provide limited options for purchasing the desired medical resource, and may not readily provide a prospective purchaser (e.g., the medical institution) with such information. The seller may simply ignore the financial position of the prospective purchaser, and offer a standard transaction option not suitable or feasible for that purchaser.

Additionally, if the seller offers a standard lease option and a standard installment loan option, the prospective purchaser may not have access to a financial analysis system suitable for evaluating the lease and loan options. Furthermore, the financial systems currently available may not be suitable for analyzing financial data associated with medical institutions, and more particularly to investment transactions in medical resources. For example, medical institutions may have specific financial data (e.g., variable and fixed costs, revenues, deductions, etc.), which is significantly different from financial data associated with other fields and industries. Even within the medical field, the specific financial data may vary greatly from institution to institution.

Accordingly, there is a need for a technique for analyzing a desired medical resource investment for a medical institution based on financial data from the medical institution, and for providing a plurality of transaction options tailored to the financial data. More particularly, there is a need for a financial analysis system allowing interactive exchange of information, such as client data and transaction options, between a remote client interface and the financial analysis system via a network.

SUMMARY OF THE INVENTION

The present technique is associated with financial analysis of a transaction for medical resources. The technique allows a client to interact with a remote financial analysis system via a network interface, and to enter and transmit client data associated with a desired transaction to the financial analysis system for a transaction analysis. The client data is utilized by the financial analysis system to tailor the transaction analysis for the particular client, or medical facility. Accordingly, the client receives multiple transaction options for the desired transaction to better serve and meet the financial needs of the client.

According to one aspect of the present technique, a method may be provided for analyzing transactions for medical resources. The method comprises providing access to a financial analysis system, and providing a network interface for communication with the financial analysis system. The network interface has a form for entering client data for medical resources. The method also comprises receiving the client data from the network interface via the network, and analyzing the client data in the financial analysis system. The method also includes providing a plurality of financial transaction options tailored to the client data, and transmitting the plurality of financial transaction options to a client via the network.

According to another aspect of the present technique, a system may be provided for analyzing resource transactions for a medical facility. The system comprises a client computer system, a transactional analysis system, and a network for coupling the client computer system to the transactional analysis system. The system also has a financial analysis module operative on the transactional analysis system for determining terms of a financial transaction based upon client data. The client computer system is configured to transmit client data for a medical facility to the financial analysis module. The financial analysis module is configured to evaluate the client data and to generate a plurality of financial transaction options tailored to the client data.

BRIEF DESCRIPTION OF THE DRAWINGS

The foregoing and other advantages of the invention will become apparent upon reading the following detailed description with reference to the drawings in which:

FIG. 6 is an exemplary query form for entering and transmitting client data from the client to the data processing center;

FIG. 7 is an exemplary transaction form for selecting medical resources desired by the client, and for transmitting client data from the client to the data processing center; and FIG. 8 is an exemplary transaction options page for displaying medical resource transaction options received by the client from the data processing center.

DETAILED DESCRIPTION OF THE INVENTION

Figure 1:
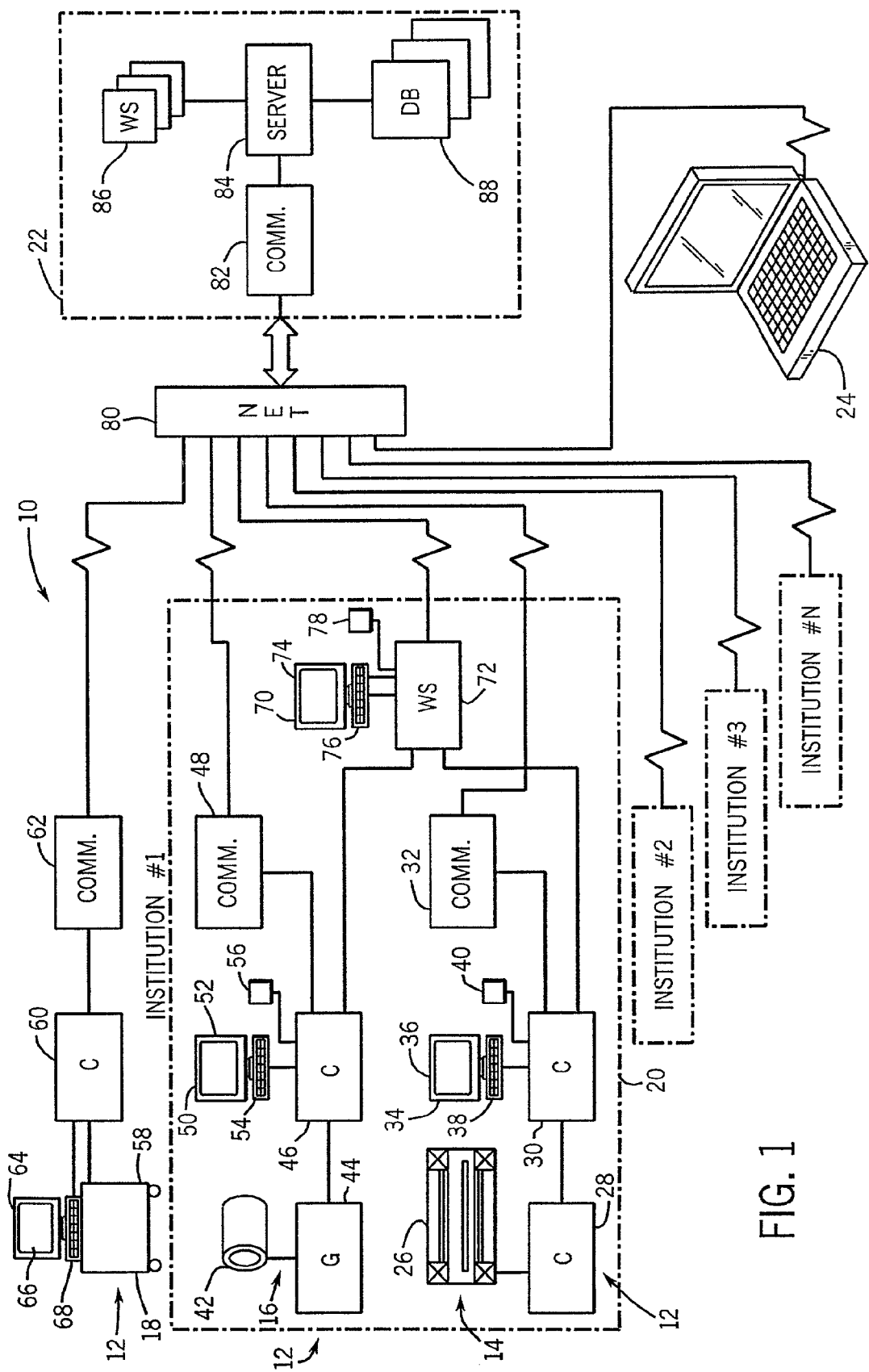
FIG. 1 is a diagram of the present technique, illustrating an exemplary system for communication and data exchange between a plurality of medical clients and a data processing center remote from the medical clients.

Turning now to the drawings, and referring first to FIG. 1, a communication system 10 is illustrated for providing remote data processing for a plurality of healthcare providers having a plurality of medical resources, such as medical diagnostic systems 12. In the embodiment illustrated in FIG. 1, the medical diagnostic systems 12 include a magnetic resonance imaging (MRI) system 14, a computed tomography (CT) system 16, and an ultrasound imaging system 18. The diagnostic systems 12 may be positioned in a single location or facility, such as institutions #1, #2, #3 and #N (e.g., medical facility 20), or may be remote from one another as illustrated for ultrasound imaging system 18. Each medical facility also may gain remote access to a data processing center 22 via the communication system 10. The data processing center 22 is also accessible via a remote client unit 24. Accordingly, multiple client workstations and medical institutions with various modalities have access to the data processing center 22.

In the exemplary embodiment of FIG. 1, several different medical clients (e.g., institutions #1, #2, #3 and #N) are provided with remote access to the data processing center 22. These and other medical clients may be provided access to, and benefit from, the data processing center 22, depending upon the capabilities of the data processing center 22, and other factors. However, the present technique is particularly well suited for remotely processing client data associated with a wide variety of medical diagnostic system modalities, including MRI systems, CT systems, ultrasound systems, positron emission tomography (PET) systems, nuclear medicine systems, and so forth. Moreover, the medical clients utilizing the data processing center 22 in accordance with the present techniques may be in different medical fields, may have different medical resources, and may have different types of patients. For example, medical resources may include a variety of medical equipment, systems, instruments and human resources for a particular medical procedure or medical practice. Furthermore, medical resources may include real estate, office space, healthcare service capacity, and financial resources of a particular institution. A variety of client data may be transmitted to the data processing center 22 via the communication system 10. For example, the client may transmit data from the medical diagnostic systems, data files from a computer, or data may be entered from a client computer coupled to the communication system 10 (e.g., remote client unit 24). The client data may comprise a variety of information associated with the client, the particular medical institution, and with the medical resources available to the particular medical institution. For example, the client data may comprise past and projected financial data/statistics, operational data/statistics, medical resources used or desired by the client, patient information, and other relevant client data from past operations or future projections.

The medical resources, as noted above, may comprise a variety of medical systems. Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. The system controller 30 includes a uniform platform for interactively exchanging client data and processing requests with data processing center 22, as described more fully below. The system controller 30 is linked to a communications module 32, which may be included in a single or separate physical package from system controller 30. System controller 30 is also linked to an operator station 34, which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally. Accordingly, it should not be limited to image data acquisition, to picture archiving communications and retrieval systems, nor to image management systems, facility or institution management systems, viewing systems and the like, in the field of medical diagnostics. More particularly, the medical resources may include imaging systems, clinical diagnostic systems, physiological monitoring systems, and so forth.

Similarly, CT system 16 will typically include a scanner 42, which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for processing at the data processing center 22. Also, the system controller 46 is coupled to an operator station 50, which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting client data and processing requests between system controller 60 and the data processing center 22. System 18 also includes an operators station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated embodiment. The management system may include a computer workstation or personal computer 72 coupled to the system controllers in an Intranet configuration, in a file sharing configuration, a client/server arrangement, or in any other suitable manner. Moreover, management station 70 will typically include a monitor 74 for viewing system operational parameters, analyzing system utilization, and exchanging client data and processing information between the facility 20 and the data processing center 22. Input devices, such as a standard computer keyboard 76 and mouse 78, may also be provided to facilitate the user interface. It should be noted that, alternatively, the management system, or other diagnostic system components, may be "stand-alone" or not coupled directly to a diagnostic system. Although the data processing center 22 may require a variety of client data to fully process a client request, the client data may not include medical system data derived directly from the medical system (e.g., CT and MRI systems). The client data may simply be transmitted from a client computer (e.g., remote client unit 24) after having been entered by the medical client. For example, the client data may be entered via an electronic form, or web interface.

The communication modules mentioned above, as well as workstation 72 and remote client unit 24, may be linked to data processing center 22 via a remote access network 80. For this purpose, any suitable network connection may be employed. Presently preferred network configurations include both proprietary or dedicated networks, as well as open networks, such as the Internet. Data may be exchanged between the institutions, medical resources, client computers and the remote data processing center 22 in any suitable format, such as in accordance with the Internet Protocol (IP), the Transmission Control Protocol (TCP), or other known protocols. Moreover, certain portions of the data may be transmitted or formatted via markup languages such as the HyperText Markup Language (HTML), Extensible Markup Language (XML), or other Internet and communication languages. Exemplary interface structures and communications components are described in detail below.

Within the data processing center 22, messages, client requests and client data are received by communication components as indicated generally at reference numeral 82. The communication components 82 direct the client data to a server, or a processing system 84, for the receipt, handling and processing of client data. In general, processing system 84 may include one or a plurality of computers, as well as dedicated hardware or software servers for processing the various requests and for receiving and transmitting the information as described more fully below. The data processing center 22 also may include a bank of workstations 86, which may be staffed by operators who address the processing requests and provide off and on-line assistance in response to the processing requests. Also, the processing system 84 may be linked to a set of databases or other processing systems 88 at or remote from the data processing center 22. Such databases and processing systems may include extensive database information on medical resources (e.g., medical systems), a particular medical facility, and so forth. As described below, such databases may be employed both for analyzing the client data and for processing the request transmitted by the client.

Figure 2:
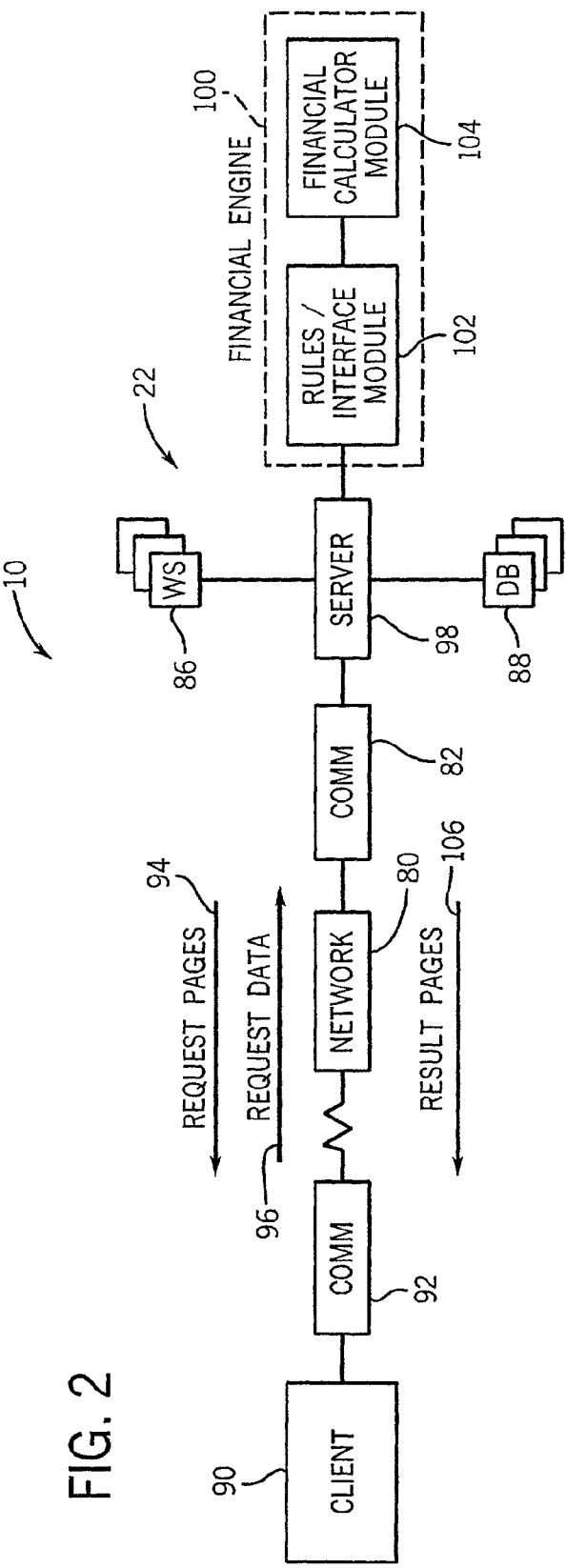
FIG. 2 is a diagram of the present technique, illustrating an exemplary embodiment of the data processing center and data exchange between the data processing center and a client.

FIG. 2 is a diagram of the communication system 10, illustrating an exemplary embodiment of the data processing center 22 accessible by a client 90. The client 90 may be a medical facility, institution or individual interested in medical resources. The data processing, center 22 may be associated with a medical supplier, a medical institution, or some other entity located remote from the client 90. For example, the data processing center 22 may be associated with a financial consulting firm, or some other financial analysis entity. The client 90 can communicate with the data processing center 22 via a communication device 92, which connects to the network 80 and the communication components 82 for the data processing center 22. The communication device 92 may be a modem or some other network device, allowing the client 90 to connect to the network 80 with a client computer system (e.g., remote client unit 24). The client 90 may access the network 80 via the Internet or other suitable network connections, thus the network 80 can be broadly interpreted to comprise all necessary networking between the client 90 and the data processing center 22.

In this exemplary embodiment, the client 90 electronically receives request pages 94 (e.g., data entry forms) from the data processing center 22, or an applications server for the network (e.g., Internet). For example, the client 90 may go to a web site having the request pages. The client 90 enters data, makes appropriate selections, and transmits a processing request to the data processing center 22. Accordingly, request data 96 is routed through the network 80 and to the data processing center 22. The request data 96 may comprise a variety of client data, as discussed above. The request data 96 is received by a server, or processing system 98, which handles the request, interprets and evaluates the request data, and provides a data analysis based on the request data. The processing system 98 may include a plurality of computer systems, servers, workstations 86, databases 88, and other hardware and software applications necessary for processing the request data.

In this exemplary embodiment, the processing system 98 has a financial engine 100 for financially analyzing the request data, and for generating a financial analysis tailored to the request data from the client. The financial engine 100 may be a remote analysis system, accessible by the processing system 98, or it may be an integral part of the processing system 98. The financial engine 100 has a rules and interface module 102 and a financial calculator module 104, which jointly work to provide a customized financial analysis for the client 90 based on the request data 96.

The rules and interface module 102 comprises rules for financially analyzing the request data, including tax rules and other considerations for the medical field. Accordingly, the rules and interface module 102 adapts the financial calculator module 104 to the desired industry or field, such as medical resources. For example, the medical field may be subject to specific taxes, laws, regulations, and various accounting and/or financial practices unlike other fields. By providing such rules, the financial calculations are customized for the medical field, enabling the financial engine 100 to more accurately analyze the client request data. Alternatively, the rules and interface module 102 may simply comprise an interface for procuring communication between the processing system 98 and the financial engine 100, particularly where the two systems are remote from one another or require translation from one system to the other (e.g., different software or communication protocols).

After analyzing the request data, the financial engine 100 provides a financial analysis tailored to the request data. Result pages 106 are then transmitted to the client 90 via the communication system 10, either directly from the financial engine 100 or after further processing by the processing system 98. For example, the processing system 98 may generate user viewable pages (e.g., Internet pages) based on the financial analysis. The client may then view the result pages via a network interface, which may comprise a client computer system having an Internet browser or other appropriate software.

Figure 3:
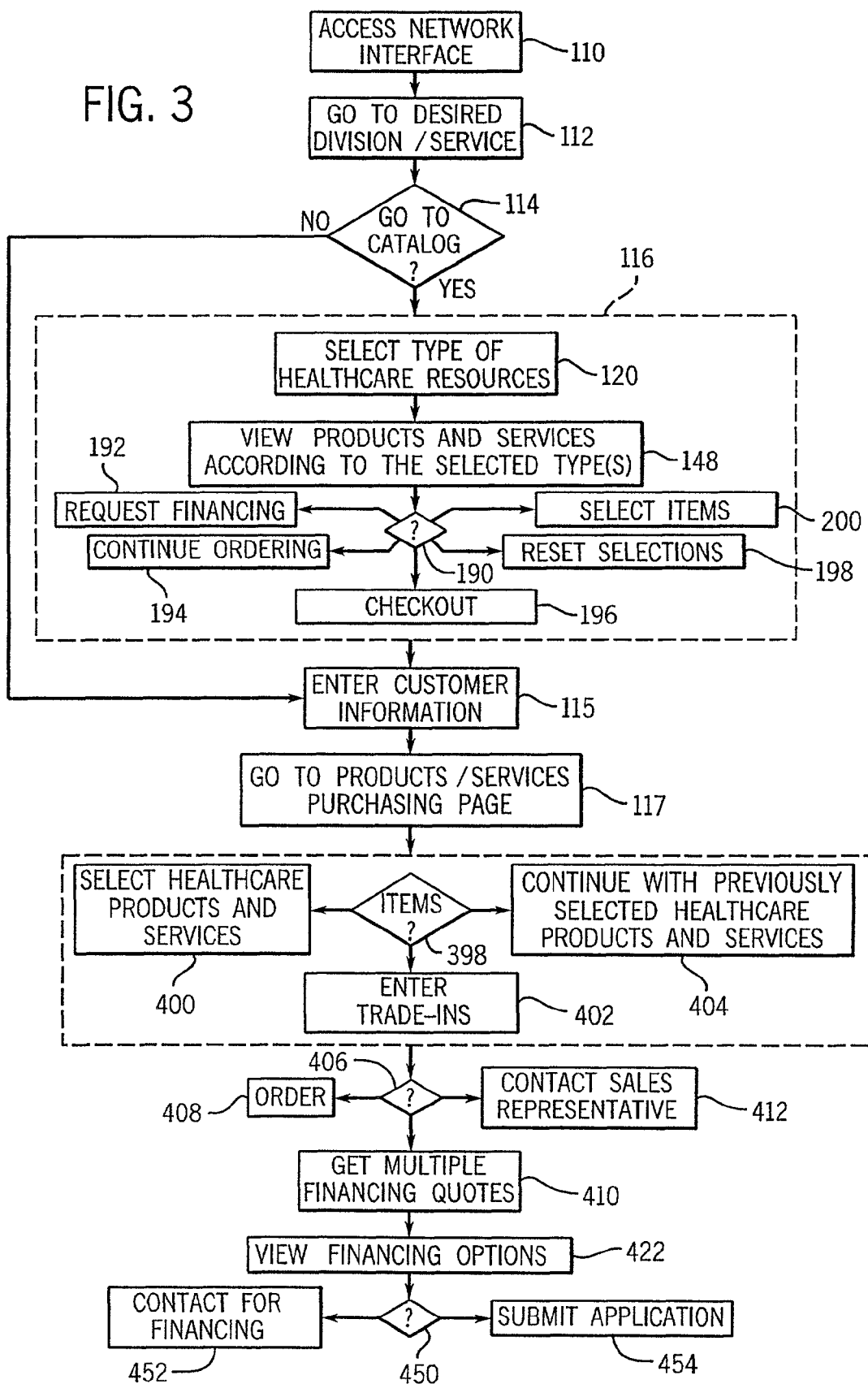
FIG. 3 is an exemplary flow chart of the present technique, with reference to the network interface pages of FIGS. 4, 5, 6, 7 and 8.

FIG. 3 is a flow chart of the present technique illustrating communication and data exchange between the client 90 and the data processing center 22. To communicate with the data processing center 22, the client 90 accesses the network interface 110, which comprises a variety of hardware and software. For example, the network interface may comprise a client computer system, a server, and communication software. An electronic form, such as those illustrated in FIGS. 4, 5, 6, 7, and 8, also may be utilized to procure client communication with the data processing center 22. For example, the network interface may be configured to access and display an Internet site (e.g., a website), requiring the client 90 to gain access to the website to view and browse the electronic forms. Accordingly, the network interface may comprise an Internet browser (e.g., Netscape or MS Internet Explorer) or other suitable software for displaying the electronic forms, provided that it allows the client 90 to transmit client data to the data processing center 22. Once the client 90 has accessed the network interface 110 (e.g. a website), which may require a password and other login information, the client 90 may browse to or go to a desired division or service 112. For example, the client 90 may browse to a particular system, service, or medical resource category at the website. The division or service may be a financial service, a productivity service, or it may be a service associated with a particular medical resource. In this exemplary embodiment, the client 90 may obtain a plurality of financing or purchasing options associated with desired medical products, systems, services and resources, based on client data. To obtain these options, the client 90 has a choice of either going to a catalog 114, or entering customer information 115 and continuing to a products and services page 117. If the client 90 wishes to select medical resources through the catalog 114, then the client 90 may browse to a query portion 116, such as query form 118 illustrated in FIG. 4.

In the present technique, the questions on the query form 118 are tailored to obtain a variety of client data, which may be relevant to an analysis of a transaction for medical resources (e.g., medical products or systems). Accordingly, the electronic forms inquire into various matters that may be relevant to a desired transaction, such as financial criteria (e.g., revenues, expenses, taxes and debt of the client 90), timing, and other factors. For example, as described below, the query form 118 may inquire into the desired medical resource, a desired time for delivery, desired options and accessories, desired warranty and service terms, and products expected to be traded in with a transaction for the medical resources. Furthermore, the query form 118 may be tailored to the client 90, or it may allow the client 90 to select the categories for data entry, rather than providing the data entry fields illustrated in FIG. 4. In one aspect, the present technique comprises a transaction analysis tool, which may be utilized by the client 90 to obtain a customized transaction analysis based on the client data. An exemplary embodiment of this transaction analysis tool utilizes the Internet, and provides an Internet based transaction analysis tool for medical clients to evaluate the desired transaction for medical resources, which may be provided/supplied by an entity hosting the transaction analysis tool.

Figures 4, 5:
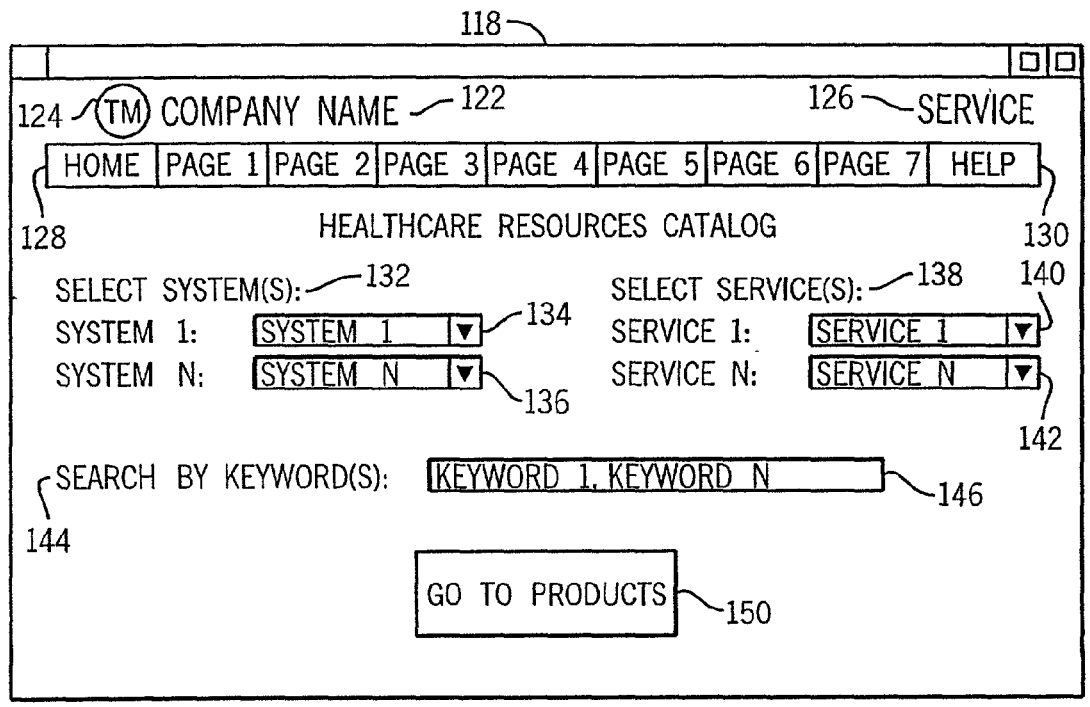
FIG. 4 is an exemplary query form for searching a catalog for a desired medical resource selected on the query form.
FIG. 5 is an exemplary results page for displaying medical resources based on the desired medical resource selected in FIG. 4.

FIG. 4 illustrates an exemplary query form 118 allowing the client 90 to select the type of health care resources 120. As illustrated, the query form 118 exhibits a company name 122, a trademark for the company 124, and a service area 126 for the company. The query form 118 also has a series of buttons or links to pages such as home 128, page 1, page 2, page 3, page 4, page 5, page 6, page 7, and help page 130. The query form 118 operates as a gateway into a medical resource catalog, allowing the client 90 to focus on one or more desired medical resources (e.g., products, systems, services, etc.). For example, the client 90 may be allowed to locate one or more medical resources by making selections in a Select Systems section 132 and/or a Select Services section 138. In the Select Systems section 132, the client 90 can select one or more medical systems (e.g., MRI & CT systems, products, equipment, instruments, etc.) from drop-down menus 134 and 136, which are provided for the client 90 to select desired medical systems 1 and N, such as SYSTEM 1 and SYSTEM N, from a list of medical systems. In the Select Services section 138, the client 90 can select one or more services 138 for service categories such as service 1 and service N (e.g., warranty, repair, maintenance, training, setup, and other services). Accordingly, drop-down menus 140 and 142 are provided for services 1 and N, respectively, allowing the client 90 to select desired medical services, such as SERVICE 1 and SERVICE N, from a list of medical services. In a Search by Keyword section 144, the client 90 can also search by keywords, by entering keywords such as KEYWORD 1 and KEYWORD N, into a text box 146. The client 90 may then search for, or view, the products and services according to the selected types 148 (e.g. the selected systems 132, selected services 138, or by keywords 144), by clicking on a button 150 labeled "Go To Products." Accordingly, the medical resource query from the query form 118 may be transmitted to, and processed on, the data processing center 22 or an applications server (e.g., a web server for a website). As the medical resource query is processed, the respective system searches for the desired medical resources in a medical resources catalog, which may comprise a resource database having a plurality of searchable field categories (e.g., system type, procedures offered by system, compatibility with other systems, system performance, price, etc.) for locating the desired medical resource.

The application server or the data processing center 22, then returns a resource results page 152 as illustrated in FIG. 5. The resource results page 152 provides a medical resource listing by product number 154, product name 156, list price 158, net price 160, and availability 162, as well as a desired quantity 164. The products 156 may comprise a System 1, a System N, Training 1, Training N, Services 1, Services N, Options 1, Options N, Accessories 1, and Accessories N, the products 156 having product numbers PN1-PN10, list prices LP1-LP10, and net prices of NP1-NP10. Each of these products 156 has an availability status 162, such as Direct Ship 166 or On Order 168. In addition, the client 90 may enter the desired quantity 164 (e.g., Q1-Q10) in fields 170 through 188, for product numbers pn1-pn10, respectively. The client 90 also has several options 190 on the resource results page 152, such as requesting financing 192, continuing to order 194, checking out 196, resetting the selections 198, and/or selecting items 200. For example, the client 90 may reset selections 198 by clicking on button 202, the client may continue ordering 194 by clicking on button 204, the client may request financing 192 by clicking on button 206, and/or the client may check out 196 by clicking on button 208. If the client 90 clicks on the Request Financing button 206 or on the Check Out button 208, then the client may be directed to one of the query forms as illustrated in FIGS. 6, 7, and 8.

Although the order of the query forms may vary, the client 90 may be directed to query form 210 for entering customer information 115, as illustrated in FIG. 6. One query form 210, the client 90 may be required to enter in a variety of customer information 115, yet the client 90 may simply be asked to enter client data for identifying the client 90 and/or for granting access to the data processing center 22. The query form 210 also may ask for customer information 115 according to customer type (e.g. an existing customer 212 and/or a new customer 214). If the client 90 is an existing customer 212, then the query form 210 may have fields 216, 218, 220, 222, 224, and a drop-down menu 226 for entering a first name 228, a last name 230, an institution name 232, an address 234, a city 236, and a state 238, such as FN1, LN1, IN1, ADDRESS1, CITY1, and state S1, respectively. For an existing customer 212, the query form 210 may also have fields 240, 242, 244, and 246 for entering a user ID 248, a password 250, a billing number 252, and/or a zip code 254, such as ID1, PW1, BN1, AND ZIP1, respectively. If the client 90 is a new customer 214, then the query form 210 may provide fields 256, 258, 260, 262, 264, and 266 for entering a first name 268, a last name 270, an institution name 272, an address 274, a city 276, and a state 278, such as FN2, LN2, IN2, ADDRESS2, CITY2, and state S2, respectively. For the new customer 214, the query form 210 may also have fields 280, 282, 284, and 286 for entering a phone number 288, an e-mail 290, a referral person 292, and a zip code 294, such as PN1, EM1, REF1, and ZIP2, respectively. Once the client 90 has entered customer information 115, the client 90 may continue to the products and services purchasing page 117 by clicking on button 296, labeled "Continue to Products".

FIG. 7 is an exemplary query form 298 for purchasing products and services 117. If the client 90 previously selected products and services from the catalog 114, then those selections are displayed in the appropriate fields of the query form 298. Otherwise, the query form 298 has query portions, entitled Equipment 300, Options and Accessories 302, Services 304, and Trade-Ins 306, for the client 90 to select the desired medical resources and trade-ins for a medical resource transaction. For each query portion 300, 302, 304, and 306, the query form 298 allows the client 90 to provide a quantity 308 and an amount 310 for the respective medical resource. For the equipment portion 300, the query form 298 provides fields 312, 314, 316, 318, 320, and 322 for entering a product/service type 324, a manufacturer 326, a model number 328, a description 330, and a desired delivery date 332, such as SYSTEM 1, MANUF 1, MODEL 1, DESC 1, and MONTH and YEAR, respectively. For the product/service type 324, the query form 298 also has fields 334 and 336 for entering the quantity 308 and the amount 310, such as Q1 and COST 1, respectively. Although the query form 298 is illustrated with only one item of equipment 300, the query form 298 may allow the client 90 to enter a plurality of products/service types 324. For example, the client 90 may select desired MRI and CT systems of particular model numbers by a desired manufacturer, and then choose a variety of servicing options and accessories to complement an order of such systems. The query form 298 also may fill the appropriate drop down menus and text boxes with model numbers, options, accessories, and services corresponding to the medical resource selected in the drop down menu 312. Thus, a selection of a CT system in drop down menu 312 may result in a list of CT options and accessories in text boxes 338 and 340.

For the query portion options/accessories 302, the query form 298 has drop-down menus 338 and 340 for entering an option 1 and an option N, such as OPTION 1 and OPTION N, respectively. The query form 298 also has text boxes 342 and 344 for entering quantities 308, such as Q2 and Q3, for the options 1 and N, respectively. Fields 346 and 348 are also provided for entering an amount 310, such as COST 2, and COST 3, for the options 1 and options N, respectively. As noted above, the drop down menus 338 and 340 may be filled with appropriate selections according to the selection made in drop down menus 312, 314 and 316 in the Equipment portion 300.

For the services query portion 304, the query form 298 may provide a plurality of service options associated with the equipment 300. For example, the query form 298 may provide drop-down menus 350, 352, and 354 for entering a training option 356, an option for a service 2, and an option for a service N, such as SERVICE PLAN 1, SERVICE PLAN 2, and SERVICE PLAN N, respectively. The query form 298 may also have text boxes 358, 360, and 362 for entering the quantity 308 (e.g. a time period for the training 356, the service 2, and the service N), such as TERM 1, TERM 2, and TERM 3, respectively. Text boxes 364, 366, and 368 are provided for entering the cost amount 310, such as COST 4, COST 5, and COST 6, for the training 356, the service 2 and the service N, respectively. If the client 90 desires to trade-in equipment 306, then the client 90 may so indicate in drop-down menus 370 and 372 and text boxes 374 and 376, which are provided for entering a product 1, a product N, an authorization number 378, and a contact name 380, such as PRODUCT 1, PRODUCT N, AUTH 1, and CONTACT 1, respectively. For products 1 and N, the query form 298 has fields 382 and 384 for entering a quantity, such as Q4 and Q5, and fields 386 and 388 for entering a trade-in amount 310, such as CREDIT 1 and CREDIT 2, respectively.

The client 90 may also select check box 390 to save the client data associated with the desired transaction displayed on the query form 298. Also, the client 90 may select check box 394 to request a financial officer to contact the client regarding the transaction displayed on the query form 298. The query form 298 may include a plurality of options such as these, utilizing check boxes or radio buttons to acquire a response from the client 90. For example, fields may be provided to inquire whether the client desires leasing options, loan options, or other arrangements for purchasing the desired medical resources.

Although the query form 298 has been described as requiring the client 90 to specifically enter in client data for the equipment 300, the options and accessories 302, the services 304, and the trade-ins 306, the query forms may be configured to automatically enter client data into the appropriate data entry fields if the client 90 previously selected the desired medical resources from the catalog 114. Accordingly, if the client 90 accesses the query form 298 after previously browsing and selecting items from the catalog, then the client 90 may either accept the previously selected items, edit the previously selected items, or add new items 398. For example, the client 90 may enter or select health care products and services 400, enter trade-ins 402, and/or continue with previously selected medical products and services 404. Once the client 90 is satisfied with the selections and/or entries on the query form 298, then the client 90 may have one of three choices 406. The client 90 may continue with an order transaction 408, request multiple financing quotes regarding the transaction 410, or contact a sales representative 412, by clicking on buttons 414, 416, or 418, respectively. For example, the Order button 414 may direct the client to an order transaction page (e.g., for entering shipping information, payment information, etc.), whereas the Contact Sales Rep. Button 418 may automatically send a contact request to a representative or it may direct the client to an e-mail screen or a contact screen (e.g., listing phone numbers, email, etc.) for contacting the representative.

If the client 90 desires to get multiple financing quotes 410, then by pressing button 416, the client 90 is directed to financing form 420 for viewing financing options 422, as illustrated in FIG. 8. As mentioned above, the client data entered into the query form 298 is transmitted to the data processing center 22, where the financial engine 100 analyzes the client data transmitted from the query form 298 and provides a plurality of financing options for display via the financing form 420. Note also, that the present technique may comprise a variety of other query forms for entering in additional client data, such as financial data corresponding to the medical facility and/or medical resources for the client 90. Accordingly, financial data from the client 90, such as described above, assists the financial engine 100 in analyzing and providing financing options better suited to the financial position of the client 90.

To provide multiple transaction options tailored to the client 90, the financial engine 100 may utilize a plurality of mathematical software applications to financially analyze the client data, and may have one or more of the rules interface modules 102. For example, the financial engine 100 may comprise a spreadsheet for laying out and analyzing the client data, a statistics program for statistically analyzing the client data, a graphics program for plotting the client data, and a web page development application for producing web pages from the client data analyzed by the data processing center 22. The rules interface module 102 also may have a tax module, a time value of money module (e.g., for evaluating a present value of cash flows), and/or a healthcare/medical module (e.g., having rules particular to the medical field or the particular client 90).

As illustrated in FIG. 8, the financing form 420 displays a plurality of financing options for a transaction desired by the client 90, with information organized by headings such as pre-approved 424, select the financing option 426, term of the financing option 428, description of the financing option 430, and payments 432 associated with the financing option. As listed under the description heading 430, the financing options may comprise an installment loan 434, an operating lease 436, an operating lease with service 438, a package 4 and/or a package N, each of which may have features tailored to the client 90 based on the client data. For example, the financing options 430 may have terms 428 (e.g., time periods) for financing, ranging from term 1 to term N, and may have financing payment amounts 432 (e.g., monthly payments in dollars) ranging from payment 1 to payment N, respectively. Also, the financing options 430 may be pre-approved, not pre-approved, under review or have some other status. After viewing the financing options 422, the client 90 may select the desired financing options 426 by selecting one or more of check boxes 440, 442, 444, 446, and/or 448, corresponding to financing packages 434, 436, 438, 4 and N, respectively. The client 90 then has options 450, such as contacting a representative for financing 452 and/or submitting an application 454 for financing the desired medical resource transaction. If the client 90 desires to contact a representative for financing 452, then the client may click on button 456 to contact a sales/financial representative, or click on button 458 to request that a financing representative contact the client 90. If the client 90 desires to submit the application 454, then the client may click on button 460 to submit the financing application. The client 90 may also print the financing quotes displayed on the financing form 420 by clicking on button 462.

In sum, the client 90 is provided a plurality of transaction or financing options tailored to the client data, allowing the client to select transaction terms best fit to the client data associated with the medical facility, medical resources, and financial position of the client 90. Accordingly, if the client 90 desires to submit an application 454, then a financing request corresponding to the selections 426 on the financing form 420 is transmitted to the data processing center 22, which processes the financing request and returns a customized financing application to the client 90 via the network interface. For example, the customized financing application may have a plurality of contract terms, such as the type of contract (e.g., a lease, sale, or installment sale), party names (e.g., lessor and lessee), subject matter of the contract (e.g., medical resources), effective date and time period for the contract, monetary terms (e.g., equipment cost or financing amount), default terms, tax benefits, interim payments, insurance terms, and a variety of other contract terms. The customized financing application also provides a signature section for the parties to sign and date the contract. Various other terms also may be tailored to the client 90, based on client data obtained from electronic forms and/or other communication systems. Altogether, the present technique provides the client 90 an integrated transaction and financing system for obtaining medical resources, and allows the client 90 more financial flexibility (e.g., multiple customized financing options) in obtaining those medical resources.

According to the embodiments illustrated in FIGS. 1-8, the present technique provides an exemplary method for analyzing transactions for medical resources in a medical facility. The method may comprise providing access to a financial analysis system (e.g., associated with a medical resource supplier) via a network, providing a network interface having a form for communication with the financial analysis system, receiving client data (e.g., associated with a transaction for medical resources) from the network interface via the network, analyzing the client data in the financial analysis system, providing a plurality of financial transaction options tailored to the client data, and transmitting the plurality of financial transaction options to a client via the network.

The present technique also may comprise identifying the client 90 and tailoring the network interface to the client 90, which may involve storing at least a portion of the client data and tailoring the form to the client 90 according to the portion of client data For example, a client profile may be stored locally, or on a web server, to assist with client identification, and/or client data (e.g., financial data from prior years) may be stored on the data processing system 22 for use in analyzing the client data associated with the transaction for medical resources. Moreover, providing the network interface may involve providing a server (e.g., an applications server or web server), providing or configuring communications hardware and software, allowing Internet access, and/or configuring a client computer system to procure communication between the client 90 and the financial analysis system.

The present technique may also involve providing medical resource availability information from the medical resource supplier to the client via the network interface. For example, the client 90 may determine if and when a desired medical system will be available, when it can ship, and/or when it can be configured by the medical resource supplier. Accordingly, the method may also comprise electronically accepting applications for purchasing medical resources via the network interface (e.g., purchasing forms displayable via an Internet browser), and electronically transmitting (e.g., returning to the client 90) a purchasing agreement tailored to the client data.

The present technique also may comprise providing a query page (e.g., with data entry fields) for selecting a medical resource category, for selecting a desired medical resource (e.g., product or system), for selecting options and accessories, and/or for entering a variety of client data (e.g., financial data). After the client 90 has entered the client data, the method may involve receiving, handling, processing and evaluating the client data, such as financial information of the client, client trade-in data, and client options associated with the transaction for medical resources. The technique may also provide financial rules (e.g., tax rules, accounting practices, etc.) for evaluating the transaction, and evaluate a variety of financial criteria such as timing and tax consequences of a transaction for the medical resources. Moreover, providing the financial transaction options may comprise providing a plurality of payment times, payment amounts, service options, payment terms and conditions, ownership options (e.g., lease, loan, installment contract, etc.) for the client purchasing the medical resources. Once the financial analysis system has analyzed the client data, the present technique may transmit the results (e.g., the plurality of financial transaction options) to the client 90 for display via the network interface.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for analyzing transactions for medical resources in a medical facility, the method comprising:
   providing access to a financial analysis system for a medical resource supplier via a network;
   providing a network interface for communication with the financial analysis system, the network interface including a form for entering client data for medical resources;
   receiving the client data from the network interface via the network, wherein receiving the client data comprises receiving client trade-in data for a purchasing transaction for medical resources;
   analyzing the client data in the financial analysis system;
   providing a plurality of financial transaction options tailored to the client data; and
   transmitting the plurality of financial transaction options to a client via the network.

2. The method of claim 1, comprising storing the client data on the financial analysis system.

3. The method of claim 1, comprising storing at least a portion of the client data on a server, and tailoring the form for the client according to the portion of client data.

4. The method of claim 1, comprising coupling the financial analysis system to the Internet, and allowing communications with the financial analysis system via an Internet browser.

5. The method of claim 1, comprising providing medical resource availability information from the medical resource supplier to the client via the network interface.

6. The method of claim 1, comprising electronically accepting applications for purchasing medical resources via the network interface.

7. The method of claim 1, comprising electronically transmitting to the client a purchasing agreement for the medical resources tailored to the client data.

8. The method of claim 1, comprising evaluating tax consequences of a transaction for the medical resources.

9. The method of claim 1, wherein receiving the client data comprises receiving financial information of the client.

10. The method of claim 1, wherein providing a plurality of financial transaction options comprises providing a plurality of payment times and payment amounts.

11. The method of claim 1, wherein providing a plurality of financial transaction options comprises providing a plurality of service options.

12. The method of claim 1, wherein providing a plurality of financial transaction options comprises providing a plurality of payment terms and ownership options for the client purchasing the medical resources.

13. The method of claim 12, comprising providing lease and loan options tailored to the client data.

14. The method of claim 1, comprising providing a query page for selecting a medical resource category.

15. The method of claim 1, comprising providing a set of financial rules for analyzing the client data.

16. A system for analyzing resource transactions for a medical facility, the system comprising:
   a client computer system for a medical facility;
   a transactional analysis system for a medical resource supplier;
   a network for coupling the client computer system to the transactional analysis system; and a financial analysis module operative on the transactional analysis system for determining terms of a financial transaction based upon client data, the client computer system being configured to transmit client data to the financial analysis module, and the financial analysis module being configured to evaluate the client data and to generate a plurality of financial transaction options tailored to the client data, wherein the client data comprises trade-in data for a client trade-in with the financial transaction.

17. The system of claim 16, wherein the financial analysis module comprises a set of financial rules.

18. The system of claim 17, wherein the set of financial rules comprises tax rules for evaluating tax consequences of the financial transaction.

19. The system of claim 16, wherein the client data comprises financial data for the medical facility.

20. The system of claim 16, wherein the client data comprises a desired healthcare category.

21. The system of claim 16, wherein the client data comprises a desired option for purchasing a medical resource.

22. The system of claim 21, wherein the desired option comprises a desired service.

23. The system of claim 16, wherein the plurality of financial transaction options comprise a loan option.

24. The system of claim 16, wherein the plurality of financial transaction options comprise a lease option.

25. The system of claim 16, wherein the plurality of financial transaction options comprise a plurality of payment amounts and payment times.

26. The system of claim 16, comprising a client interface configured for exchanging information and procuring a financial transaction between the medical facility and the medical resource supplier via the network.

27. The system of claim 26, wherein the client interface comprises at least one page for displaying the plurality of financial transaction options.

28. The system of claim 26, wherein the client interface comprises a transaction agreement page tailored to the client data.

29. The system of claim 28, wherein the transaction agreement page comprises a loan agreement according to one of the plurality of financial transaction options.

30. The system of claim 28, wherein the transaction agreement page comprises a lease agreement according to one of the plurality of financial transaction options.

31. A method for facilitating a purchasing transaction between a medical resource supplier and a client, the method comprising:
providing access to a transaction system for a medical resource supplier via a network;
providing an interface for exchanging information between a client and the transaction system, wherein the interface has fields for entering client data;
receiving the client data from the interface via the network, wherein receiving the client data comprises receiving client trade-in information for a purchasing transaction for medical resources;
financially analyzing at least a portion of the client data with a financial analysis system operative on the transaction system;
generating a plurality of purchasing options tailored to the client data; and
transmitting the plurality of purchasing options to the client via the network, wherein the plurality of purchasing options comprise lease and loan options.

32. The method of claim 31, comprising coupling the transaction system to the Internet.

33. The method of claim 31, comprising electronically transmitting to the client a purchasing agreement for medical resources tailored to the client data.

34. The method of claim 31, comprising evaluating tax consequences of a purchasing transaction for medical resources according to the client data.

35. The method of claim 31, wherein receiving the client data comprises receiving financial information of the client.

36. The method of claim 31, wherein generating a plurality of purchasing options comprises providing a plurality of service options.

37. A method for providing medical resources to a medical facility, the method comprising:
providing access to a financial module for a medical resource supplier via a network;
providing a communication interface comprising fields for transmitting client data to the financial module, wherein the client data includes a medical system category;
receiving client trade-in information at the financial module;
financially analyzing at least a portion of the client data with the financial module;
generating a plurality of transaction options tailored to the client data; and
transmitting the plurality of transaction options to a client via the network.

38. The method of claim 37, comprising electronically transmitting to the client a purchasing agreement for medical resources tailored to the client data.

39. The method of claim 37, comprising evaluating tax consequences of a purchasing transaction for medical resources according to the client data.

40. The method of claim 37, comprising receiving financial information of the client at the financial module.

41. The method of claim 37, wherein generating a plurality of transaction options comprises providing a plurality of service options.

42. The method of claim 37, wherein generating a plurality of transaction options comprises providing a plurality of payment terms and ownership options.

43. The method of claim 37, wherein generating a plurality of transaction options comprises providing lease and loan options tailored to the client data.

44. The method of claim 37, comprising displaying the plurality of transaction options on the communication interface.

45. A method for analyzing transactions for medical resources in a medical facility, the method comprising:
providing access to a financial analysis system for a medical resource supplier via a network;
providing a network interface for communication with the financial analysis system, the network interface including a form for entering client data for medical resources;
receiving the client data from the network interface via the network;
analyzing the client data in the financial analysis system;
providing a plurality of financial transaction options comprising a lease option tailored to the client data; and
transmitting the plurality of financial transaction options to a client via the network.

46. A method for analyzing transactions for medical resources in a medical facility, the method comprising:
providing access to a financial analysis system for a medical resource supplier via a network;

providing a network interface for communication with the financial analysis system, the network interface including a form for entering client data for medical resources;

receiving the client data from the network interface via the network;

analyzing the client data in the financial analysis system;

providing a plurality of financial transaction options comprising a loan option tailored to the client data; and transmitting the plurality of financial transaction options to a client via the network.

47. A system for analyzing resource transactions for a medical facility, the system comprising:

a client computer system for a medical facility;

a transactional analysis system for a medical resource supplier;

a network for coupling the client computer system to the transactional analysis system; and a financial analysis module operative on the transactional analysis system for determining terms of a financial transaction based upon client data, the client computer system being configured to transmit client data to the financial analysis module, and the financial analysis module being configured to evaluate the client data and to generate a plurality of financial transaction options tailored to the client data, wherein the plurality of financial transaction options comprise a lease option.

48. A system for analyzing resource transactions for a medical facility, the system comprising:

a client computer system for a medical facility;

a transactional analysis system for a medical resource supplier;

a network for coupling the client computer system to the transactional analysis system; and a financial analysis module operative on the transactional analysis system for determining terms of a financial transaction based upon client data, the client computer system being configured to transmit client data to the financial analysis module, and the financial analysis module being configured to evaluate the client data and to generate a plurality of financial transaction options tailored to the client data, wherein the plurality of financial transaction options comprise a loan option.

49. A method for facilitating a purchasing transaction between a medical resource supplier and a client, the method comprising:

providing access to a transaction system for a medical resource supplier via a network;

providing an interface for exchanging information between a client and the transaction system, wherein the interface has fields for entering client data;

receiving the client data from the interface via the network;

financially analyzing at least a portion of the client data with a financial analysis system operative on the transaction system;

generating a plurality of purchasing options tailored to the client data, wherein the plurality of purchasing options comprise a lease option; and transmitting the plurality of purchasing options to the client via the network.

50. A method for facilitating a purchasing transaction between a medical resource supplier and a client, the method comprising:

providing access to a transaction system for a medical resource supplier via a network;

providing an interface for exchanging information between a client and the transaction system, wherein the interface has fields for entering client data;

receiving the client data from the interface via the network;

financially analyzing at least a portion of the client data with a financial analysis system operative on the transaction system;

generating a plurality of purchasing options tailored to the client data, wherein the plurality of purchasing options comprise a loan option; and transmitting the plurality of purchasing options to the client via the network.

51. A method for providing medical resources to a medical facility, the method comprising:

providing access to a financial module for a medical resource supplier via a network;

providing a communication interface comprising fields for transmitting client data to the financial module, wherein the client data includes a medical system category;

financially analyzing at least a portion of the client data with the financial module;

generating a plurality of transaction options tailored to the client data, wherein generating a plurality of transaction options comprises providing lease and loan options tailored to the client data; and transmitting the plurality of transaction options to a client via the network.

52. A program for facilitating a purchasing transaction between a medical resource supplier and a client, comprising:

a non-transitory machine readable medium; and machine readable code disposed on the non-transitory machine readable medium and adapted for:

providing access to a transaction system for a medical resource supplier via a network;

providing an interface for exchanging information between a client and the transaction system, wherein the interface has fields for entering client data;

receiving the client data from the interface via the network, wherein receiving the client data comprises receiving client trade-in information for a purchasing transaction for medical resources;

financially analyzing at least a portion of the client data with a financial analysis system operative on the transaction system;

generating a plurality of purchasing options tailored to the client data; and transmitting the plurality of purchasing options to the client via the network, wherein the plurality of purchasing options comprise lease and loan options.

53. A program for facilitating a purchasing transaction between a medical resource supplier and a client, comprising:

a non-transitory machine readable medium; and machine readable code disposed on the non-transitory machine readable medium and adapted for:

providing access to a transaction system for a medical resource supplier via a network;

providing an interface for exchanging information between a client and the transaction system, wherein the interface has fields for entering client data;

receiving the client data from the interface via the network;

financially analyzing at least a portion of the client data with a financial analysis system operative on the transaction system;

generating a plurality of purchasing options tailored to the client data, wherein the plurality of purchasing options comprise a lease option; and transmitting the plurality of purchasing options to the client via the network.

54. A program for facilitating a purchasing transaction between a medical resource supplier and a client, comprising:
a non-transitory machine readable medium; and
machine readable code disposed on the non-transitory machine readable medium and adapted for:
providing access to a transaction system for a medical resource supplier via a network;
providing an interface for exchanging information between a client and the transaction system, wherein the interface has fields for entering client data;
receiving the client data from the interface via the network;
financially analyzing at least a portion of the client data with a financial analysis system operative on the transaction system;
generating a plurality of purchasing options tailored to the client data, wherein the plurality of purchasing options comprise a loan option; and
transmitting the plurality of purchasing options to the client via the network.

55. A program for providing medical resources to a medical facility, comprising:
a non-transitory machine readable medium; and
machine readable code disposed on the non-transitory machine readable medium and adapted for:
providing access to a financial module for a medical resource supplier via a network;
providing a communication interface comprising fields for transmitting client data to the financial module, wherein the client data includes a medical system category;
receiving client trade-in information at the financial module;
financially analyzing at least a portion of the client data with the financial module;
generating a plurality of transaction options tailored to the client data; and
transmitting the plurality of transaction options to a client via the network.

56. A program for providing medical resources to a medical facility, comprising:
a non-transitory machine readable medium; and
machine readable code disposed on the non-transitory machine readable medium and adapted for:
providing access to a financial module for a medical resource supplier via a network;
providing a communication interface comprising fields for transmitting client data to the financial module, wherein the client data includes a medical system category;
financially analyzing at least a portion of the client data with the financial module;
generating a plurality of transaction options tailored to the client data, wherein generating a plurality of transaction options comprises providing lease and loan options tailored to the client data; and
transmitting the plurality of transaction options to a client via the network.

* * * * *